US00PP36619P3

(12) United States Plant Patent
Martin

(10) Patent No.: US PP36,619 P3
(45) Date of Patent: Apr. 22, 2025

(54) ***CANNABIS* PLANT NAMED 'GPZ'**

(50) Latin Name: *Cannabis sativa*
Varietal Denomination: GPZ

(71) Applicant: Umami Worldwide, LLC, Las Vegas, NV (US)

(72) Inventor: Chase Martin, Las Vegas, NV (US)

(73) Assignee: UMAMI WORLDWIDE, LLC, Las Vegas, NV (US)

( * ) Notice: Subject to any disclaimer, the term of this patent is extended or adjusted under 35 U.S.C. 154(b) by 0 days.

(21) Appl. No.: 17/950,097

(22) Filed: Sep. 22, 2022

(65) Prior Publication Data

US 2023/0088108 A1 Mar. 23, 2023
US 2023/0088108 A1 Mar. 23, 2023

Related U.S. Application Data

(60) Provisional application No. 63/247,292, filed on Sep. 22, 2021.

(51) Int. Cl.
*A01H 5/02* (2018.01)
*A01H 6/28* (2018.01)

(52) U.S. Cl.
USPC ..... Plt./258

(58) Field of Classification Search
USPC ..... Plt./258, 263.1
CPC ... A01H 5/02; A01H 5/12; A01H 5/00; A01H 6/28
See application file for complete search history.

(56) References Cited

U.S. PATENT DOCUMENTS

PP35,667 P3 * 2/2024 Martin ..... A01H 6/28 Plt./258
PP35,689 P3 * 3/2024 Martin ..... A01H 6/28 Plt./258
PP35,690 P3 * 3/2024 Martin ..... A01H 6/28 Plt./258

* cited by examiner

*Primary Examiner* — June Hwu
(74) *Attorney, Agent, or Firm* — Leonard R. Svensson; Intelink Law Group, PC

(57) ABSTRACT

The *Cannabis* cultivar 'GPZ' can be briefly characterized by massive purple, red, white, green, and yellow streaking resin-coated flowers with a distinct spiked golf ball flower structure on lower bud sites with a central spear shaped cola. 'GPZ' grows large and dense flower clusters and very short internodal space.

2 Drawing Sheets

Latin name of the genus and species: *Cannabis sativa.*
Variety denomination: 'GPZ'.

BACKGROUND OF THE INVENTION

The present invention relates to a new and distinct *Cannabis* cultivar designated 'GPZ'. This new cultivar is the result of controlled-crosses between proprietary cultivars made by the inventors. 'GPZ' was asexually produced in Orange, CA via stem cuttings and cloning method by the inventor. Asexual clones have been grown and tested indoors and in greenhouses and the properties are found to be transmissible by such asexual reproduction. The cultivar and its traits are stable through many generations of asexual propagation.

TAXONOMY AND NOMENCLATURE

*Cannabis*, more commonly known as marijuana, is a genus of flowering plants that includes at least three species, *Cannabis sativa, Cannabis indica*, and *Cannabis ruderalis* as determined by plant phenotypes and secondary metabolite profiles. In practice however, *Cannabis* nomenclature is often used incorrectly or interchangeably. *Cannabis* literature can be found referring to all *Cannabis* varieties as "*sativas*" or all cannabinoid producing plants as "*indicas*". Indeed, the promiscuous crosses of indoor *Cannabis* breeding programs have made it difficult to distinguish varieties, with most *Cannabis* being sold in the United States having features of both *sativa* and *indica* species.

Human cultivation history of *Cannabis* dates back 8000 years (Schultes, R E., 1970, Random thoughts and queries on the botany of *Cannabis*. Pages 11-38 in: C R B Joyce, and S H Curry eds., THE BOTANY AND CHEMISTRY OF *CANNABIS*. J. & A. Churchill. London, England). Hemp cloth recovered in Europe dates back 6000 years (Small, E, Beckstead, H D, and Chan, A, 1975, The evolution of cannabinoid phenotypes in *Cannabis*, ECONOMIC BOTANY 29(3):219-232). The written record of the pharmacologic properties of *Cannabis* goes back more than 4000 years (Ti, H. 2737 B C. NEI JING SU WEN HUANG TI, Yellow Emperor's Classic on Internal Medicine; referred to without citation in Small et al. 1975 Supra).

The taxonomy and nomenclature of the highly variable genus *Cannabis* (Emboden, W A, 1974, ECONOMIC BOTANY 28(3):304-310; Small, E and Cronquist, A, 1976, TAXON 25(4):405-435; Small E and Cronquist, A, 1977, TAXON 26(1):110; Hillig, K W and Mahlberg, P G, 2004, American Journal of Botany 91(6):966-975), remains in question. This is in spite of the fact that its formal scientific name, '*Cannabis sativa* L.', assigned by Carolus Linneaus (Linnaeus, C, 1753, SPECIES PLANTARUM, 2:1027, Salvius, Stockholm, Facsimile edition, 1957-1959, Ray Society, London, U.K.), is one of the oldest established names in botanical history and is still accepted to this day. Another species in the genus, '*Cannabis indica* Lam.' was formally named somewhat later (de Lamarck, J B, 1785, ENCYCLOPEDIE METHODIQUE DE BOTANIQUE, 1(2):694-695), but is still very old in botanical history. In 1785, Jean-Baptiste Lamarck published a description of a second species of *Cannabis*, which he named *Cannabis indica*. Lamarck based his description of the newly named species on plant specimens collected in India. *C. indica* was described as relatively short, conical, and densely branched, whereas *C. sativa* was described as tall and laxly branched (Schultes R. E. et al, 1974, Harvard University Botanical Museum Leaflets, 23:337-367). *C. indica* plants were also described as having short, broad leaflets whereas those of *C. sativa* were characterized as relatively long and narrow (Anderson L. C., 1980, Harvard University Botanical Museum Leaflets, 28:61-69). *C. indica* plants conforming to Schultes' and Anderson's descriptions may have originated from the Hindu Kush mountain range. Because of the often harsh and variable (extremely cold winters, and warm summers) climate of those parts, *C. indica* is well-suited for cultivation in temperate climates.

Three other species names were proposed in the 1800s to distinguish plants with presumably different characteristics (*C. macrosperma* Stokes, *C. chinensis* Delile, *C. gigantean* Vilmorin), none of which are accepted today, although the epithet "*indica*" lives on as a subspecies of *C. sativa* ('*C. sativa* ssp. *indica* Dam.', Small and Cronquist 1976 Supra).

In the 20th century, two new names were added to the 50 liturgy of proposed *Cannabis* species: *C. ruderalis* Janischevsky and a hybrid, x *C. intersita* Sojak. (Small, E, Jui, P Y, and Lefkovitch, L P, 1976, SYSTEMATIC BOTANY 1(1): 67-84; Small and Cronquist 1976 Supra). Further, numerous names have been proposed for horticultural variants of *Cannabis* but as of 1976, "very few of these have been validly published as formal taxa under the International Code of Botanical Nomenclature" (Small and Cronquist 1976 Supra). Moreover, other recent work continues to focus on higher-order evolutionary relationships of the genus. *Cannabis* has been variously ascribed as belonging to mulberry family (Moraceae) (Engler, H G A, Ulmaceae, Moraceae and Urticaceae, pages 59-118 in: A. Engler and K. Pranti eds., 1889, DIE NATURLICHEN PFLANZENFAMILIEN 3(1). W. Engelmann, Leipzig, Germany; Judd, W S, Sanders, R W, and Donoghue, M J, 1994, HARVARD PAPERS IN BOTANY 5:1-51; Humphries, C J and Blackmore, S, A review of the classification of the Moraceae, pages 267-277 In: Crane and Blackmore 1989 id.); nettle family (Urticaceae) (Berg, C C, Systematics and phylogeny of the Urticales, pages 193-220, in: P. R. Crane and S. Blackmore eds., 1989, EVOLUTION, SYSTEMATIC, AND FOSSIL HISTORY OF THE HAMAMELIDAE, VOL. 2, HIGHER HAMAMELIDAE, Clarendon Press, Oxford, U.K.); and most recently in its own family with hops (Humulus), Cannabaceae, or hemp family (Sytsma, K J, et al, 2002, AMERICAN JOURNAL OF BOTANY 89(9): 1531-1546). While the work of Small and Cronquist 1976 Supra, seemed to effectively confine the genus to a single species with 2 subspecies (*C. sativa, C. sativa. indica*), each with two varieties (*C. sativa* var. *sativa, C. sativa* subsp. *spontanea; C. sativa indica* var. *indica, C. sativa indica* var. Kafiristanica) largely on the basis of chemotaxonomy and infertility of all forms, more recent work (Sytsma et al. 2002 Supra), proposes a two-species concept, resurrecting the binomial *C. indica* Lam. Since Sytsma et al. (2002) provides no key for discriminating between the species, the dichotomous key of Small and Cronquist (1976), which accounts for all forms in nature, whether wild or domesticated, is preferred to classify the characteristics of the plants.

BRIEF SUMMARY OF THE INVENTION

The present invention relates to a new and distinct *Cannabis* cultivar designated 'GPZ'.

This invention relates to a new and distinctive *Cannabis* cultivar designated as 'GPZ'. 'GPZ' cultivar is a mix of *Cannabis* genetics from both northern and southern California. The father is a proprietary male plant called, Zuchi (U.S. Plant Pat. No. 35,689). The mother plant is a polyhybrid cross of Bacio Gelato, Motorbreath #15, Bubba Kush and Animal Cookies. (Applicant is not aware that the mother plant is patented in the United States or is the subject of a pending patent application in the United States.) A single plant was selected from a population of 250 seedlings. The plants were grown and flowered indoors, in a tightly controlled environment, under mixed spectrum light conditions in order to see maximum genetic expression. GPZ is asexually produced in Orange County CA via stem cuttings and cloning method by the inventor. Asexual clones have been tested indoors and in greenhouses and the properties are found to be transmissible by such asexual reproduction.

'GPZ' produces massive deep red and purple, blue, green, and white streaking resin-coated flowers with a distinct golf ball flower structure on lower bud sites with a central spear shaped cola. GPZ grows large and dense flower clusters and very short internodal space, this cultivar is able to produce very high yields for both flower and resin production It is a very hardy plant that is both drought and bug resistant, and can grow as much as 1.5-2+ inches per day with proper feed and environment.

'GPZ', unlike either parent, has a much higher degree of tolerance to insects, particularly spider mites and thrips. It is also very tolerant to molds and mildew showing zero contamination in a greenhouse with regular nights reaching over 90% RH for 10-12 hours each night. The growth pattern for rooting and branching is 1.5× faster, resulting in a higher yield within the same footprint. The scent and flavor of the finished product is much stronger and longer lasting than either parent and the side effects of inhalation are much more complex and intense than the mother plant. In addition, the selected plant expresses a higher concentration of anthocyanins present in both the leaves and stems as well as the harvested flowers. Onset of anthocyanins occurs several weeks sooner than either parent regardless of external temperature. Additionally, the cannabinoid and terpene levels are much higher than either parent as shown below. 'GPZ' unlike its parents or other plant patents (such as co-pending plant patent applications 'AFZ', now U.S. Plant Pat. No. 35,667, or 'TZT', now U.S. Plant Pat. No. 35,690) is able to maintain a consistent yield of over 120 grams per ft2 with an average flowering time of 60 days. 'GPZ' contains a higher and more complex terpene analysis at 4.407% as well as a higher cannabinoid analysis of 43.8330%. In addition, 'GPZ' has shown a greater diversity of minor cannabinoids such as THCVA 0.3188% CBCA 0.04056% and CBGA 1.0461%

The below results are from an analysis of 1 selected phenotype for the claimed plant.

The cannabinoids and terpene analysis are from the dry flower of the selected plant. The method used was High-performance liquid and gas chromatography, otherwise known as HPLC and GCMS. The standard analytical method for these compounds.

Chemical Profile:

MAX CANNABINOIDS 43.8330%
THC 0.5021%
THCA 41.3516%
THCVA 0.3188
CBDA 0.1095
CBD None Detected
CBCA 0.04056%
CBG 0.0993%
CBGA 1.0461%

Terpenes;

MAX TERPENES: 4.407%
beta-Citronellol 0.004%
Germacrene B 0.821%
Fenchol 0.095%
Selina-3, 7(11)-diene 0.096%
Camphene 0.031%
beta-Myrcene 0.152%
Phellandrenes 0.010%
3-Carene 0.008%
Eucalyptol 0.011%
Ocimenes 0.105%
Camphor 0.014%
Isoborneo1 0.008%
DL-Menthol 0.009%
Geranyl acetate 0.017%
beta-(−)-trans-Caryophyllene 0.239%
Farnesene 0.390%
Valencene 0.094%
(−)-Caryophyllene oxide 0.014%
(+)-Cedrol 0.012%
(%31 )-alpha-Bisabolol 0.029%
alpha-Pinene 0.123%
Sabinene 0.008%
alpha-Terpinene 0.009%
gamma-Terpinene 0.009%
Sabinene hydrate 0.011%
Fenchone 0.011%
(1R)-endo-(+)-Fenchyl alcohol 0.085%
(+)-Pulegone 0.011%
alpha-Humulene 0.062%
trans-Nerolidol 0.196%
Guaiol 0.010%
beta-Pinene 0.202%
p-Cymene 0.002%
(R)-(+)-Limonene 1.009%
Terpinolene 0.012%
Linalool 0.248%
Borneo1 0.021%
(−)-alpha-Terpineol 0.092%
Geraniol 0.013%
cis-Nerolidol 0.029%
beta-Eudesmol 0.027%
Phytol I 0.006%
Phytol II 0.049%

DETAILED BOTANICAL DESCRIPTION

Figure 1:
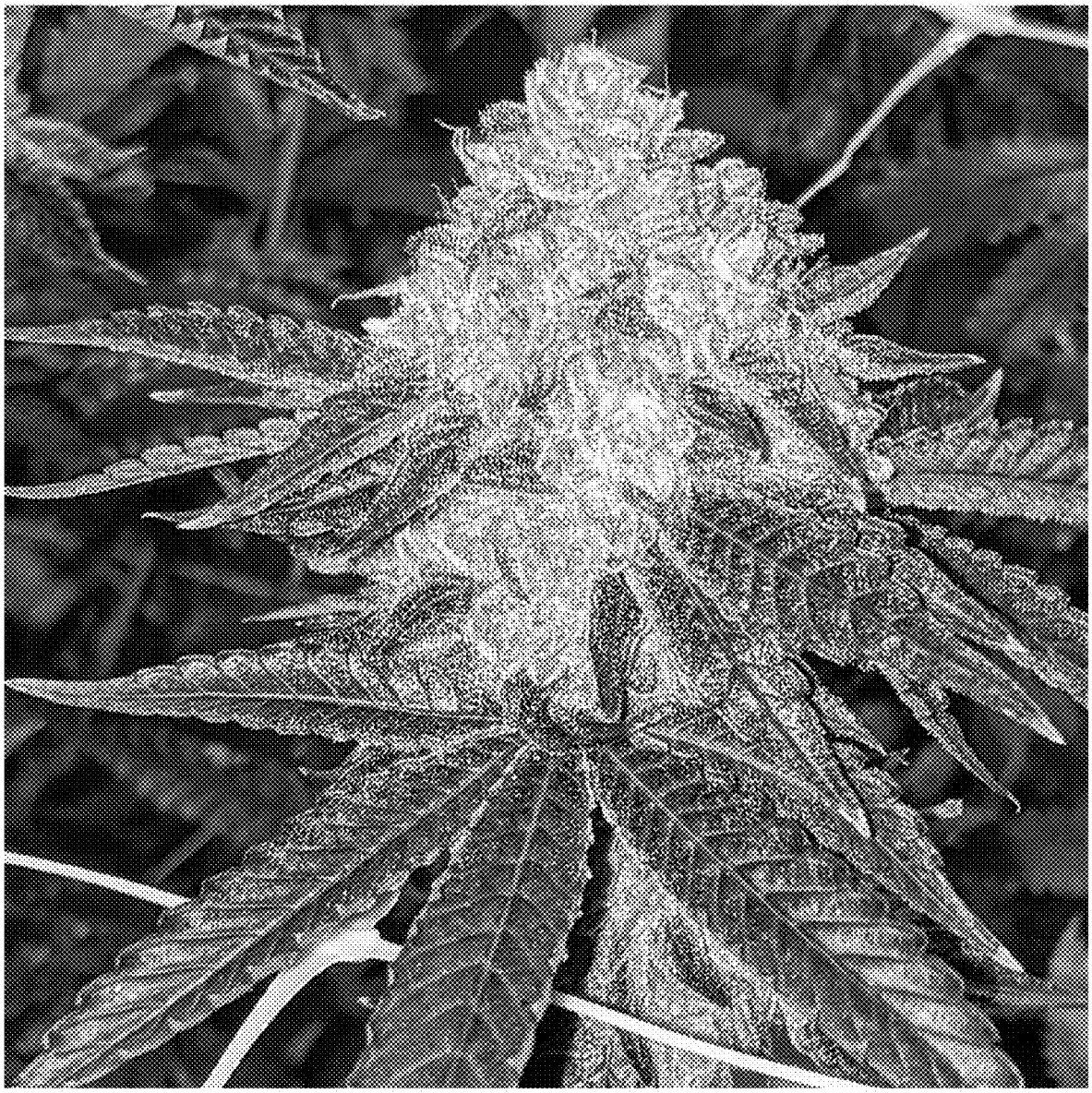
FIG. 1 is a view of a 'GPZ' flower cluster.
Figure 2:
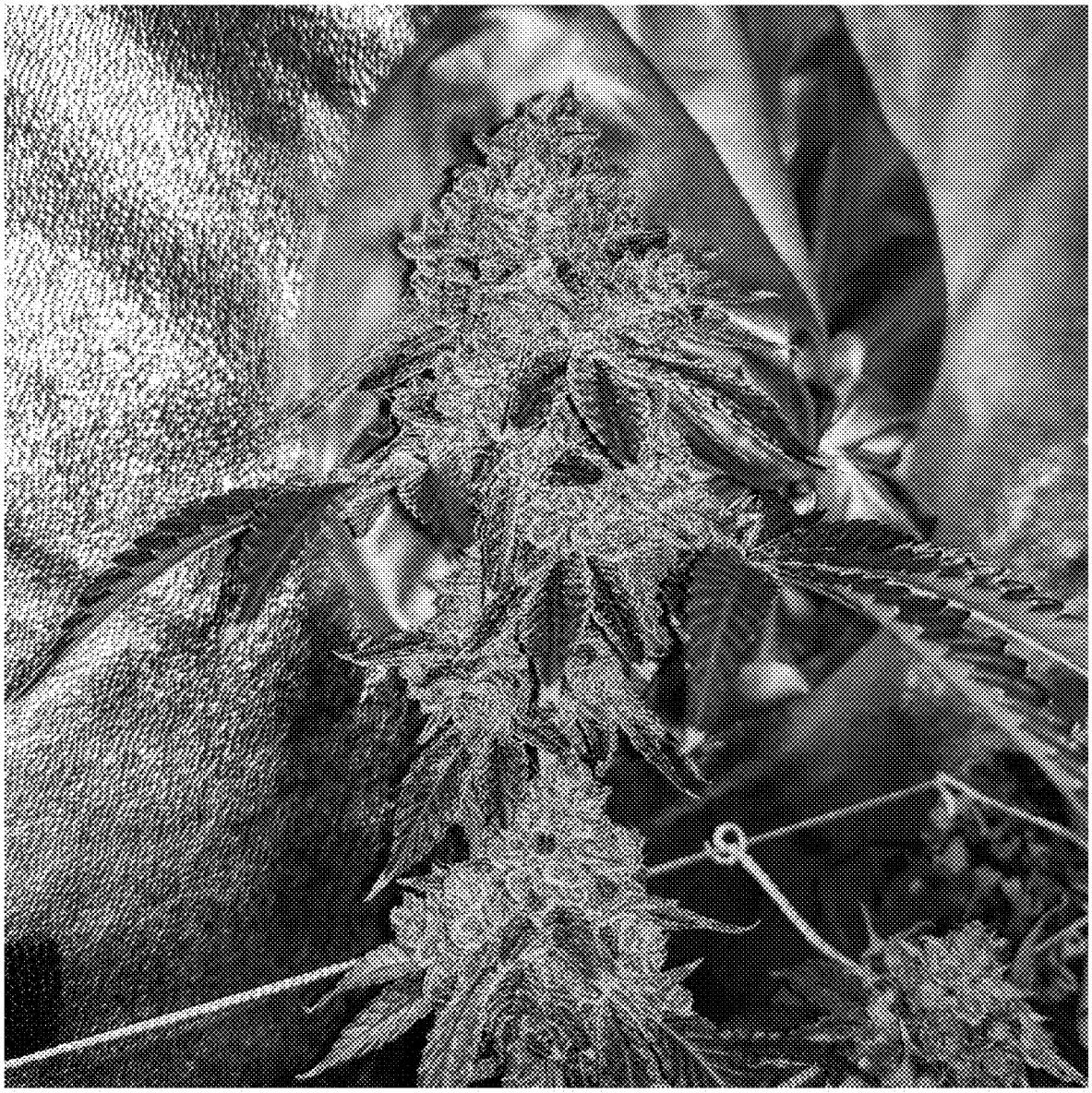
FIG. 2 is a view of several 'GPZ' flower clusters on a growing 'GPZ' plant.

'GPZ' has not been observed under all possible environmental conditions, and the phenotype may vary significantly with variations in environment. The following observations, measurements, and comparisons describe this plant as grown in Victoria, BC when grown indoors under 1500 ppfd of LED. The new plant reproduces true to type with all of the characteristics, as herein described, firmly fixed and retained through successive generations of such asexual propagation. The claimed plant expresses a very unique terpene profile and high levels of minor cannabinoids including THCV and CBC, these minor cannabinoids were confirmed via HPLC analysis The selected plants express a shorter internodal length that allows for more flower sites within the same area, resulting in a larger overall yield of flower or resin reaching up to 120 grams per ft2 in an indoor grow environment.

The color chart referenced is standard hexadecimal Web Pantone Color Chart well known to those of ordinary skill in Internet web site design.

The plant:

*Seeds*.—The seeds are round/oval in shape with large zigzag striped patterns that cover the length of the seed. They are grayish brown PMS 1265 with strong marbling and they can weigh between 0.1-0.2 g each.

*Inflorescence*.—The flowers are bulbous at the base and emerge outward creating many sharp points. The % of male vs female plants was approximately 65% female and 35% males in the selection process. There was <2% hermaphrodite expression from seed and after taking clones, the hermaphroditic expression was not seen again. The flowers are arranged in a spiral pattern up the stem similar to Brussels sprouts with each flower being fully formed and not contributing to a homogeneous "cola" shape with an average of 15 flower clusters per branch and a total of 90 flowers per plant. The average flower diameter is 1.5-2.5" when dry and as much as 4.5" when freshly harvested at 63 days after initiating flowering. The flowers develop many colors during weeks 6-9 including yellow PMS 386, vibrant purples PMS 246 and 248 PMS 262 C, red PMS 228 and pms 2726c at harvest with the stem staying very light vibrant green PMS 364. The fragrance is that of lime corn chips, sweet gas/petrol and fresh baked croissant pastry. The average flowering time is 58-63 days indoors and the first or second week of October outdoors.

*Leaves*.—The fan leaves are large and stout. They can be 7-11" long and have a total width of 6-8" with some overlap between every leaflet. The trichomes are mostly capitate stalked and are wet but sandy gritty to the touch, releasing a heavy aroma of lime corn chips, sweet gas/petrol and fresh baked croissant pastry. Leaflet shape is a long oval with ripples on all sides, they do not lie flat, the leaflet apex is very pointed and the base is rounded. An average number of leaflets is between 5-7 depending on the total plant size and health. During vegetative growth the top of the leaf is dark green PMS 347 with the bottom being light green PMS 361. During the flowering phase, the colors shift as anthocyanin is produced and leaves will develop yellow PMS 386, vibrant purples PMS 246 and 248, red PMS 228 and pms 2726c. Trichome production is found primarily on leaves that emerge from the flowers with shorter petiole length of 3" or less, these trichomes are primarily capitate stalked with Capitate-sessile on both the top and bottom of the leaf surface.

*Petioles*.—Typically 2.2-4.5" long and 0.25-0.5" in diameter. The longer and older petioles will show anthocyanin production PMS 247 starting closer to the stem and moving out toward the leaf rachis. Petioles are typically dark green PMS 357 and host primarily cystolythic trichomes. The shorter petioles that are closer to the flowers will have both Capitate-sessile and cystolythic trichomes.

*Trichomes*.—Are glandular with capitate stalked visible and bulbous trichomes and capitate-sessile all around.

*Stems*.—The stem shape is a large oval that grows very straight with little outward growth. The typical internode length is 2" when grown under 1500 ppfd of LED light. The stem is round and can reach a diameter of 1.5-3" when grown with a shallow groove depth and thick pith presence. There are no visible trichomes growing on the stem. Stem color is green PMS 368.

*Bract*.—The bract is 0.15" in diameter and 0.25" in length with 2 stigmas emerging from the center. They are covered with capitate-stalked trichomes and also house cystolythic and capitate-sessile trichomes throughout. Light green color PMS 360.

*Bracteole*.—Usually between 0.12-0.125" in length. They are slender spear-shaped and light green PMS 360.

*Stigma*.—The stigma is white PMS 11-0601 TCX and starts to turn a light orange PMS 142 as the plants dry at harvest. Average length is 0.25"

*Style*.—The style is very light green pms 358 and is oval shaped with an average length of 1.05 mm

*Height*.—The average height can be modified depending on the volume of growing media and the irrigation frequency. In a 6×6×6 rockwool cube, being fed 1500-2000 ml per day a plant will average around 36-48" in height. The selected plant is grown in clusters with 9 plants per 16 ft2. An incredibly vigorous plant, clones will take between 6-8 days to show roots and will reach a height of 17-21" after only 17-21 days.

*Stipules*.—Found at each node and are usually between 0.2-0.3" in length. They are spear-shaped and sometimes accompanied by white pistils regardless of the light cycle or season and are light green PMS 360.

*Pest and disease resistance*.—'GPZ' has shown to be incredibly resistant to insect pressure and pests, specifically spider mites (*Tetranychus urticae*) and thrips (*Thysanoptera*). 'GPZ' has also shown to be highly resistant to gray mold (*Botrytis cinerea*) and powdery mildew (*Oidiopsis taurica*) in both greenhouse and indoor environments.

*Growth conditions*.—The plants are grown and are meant to be grown in a tightly controlled environment. They have been able to withstand temperatures above 110 degrees F. with 30% RH, as well as 40 degrees F. and 95% RH

*Market use*.—The market use for this product is medical and recreational *Cannabis* flower as well as extracts and infused goods. Individual plants grown with the above methods yield an average of 3000 g at harvest resulting in a dry flower weight of up to 200 grams.

*Type* (*life form and habit*).—Herbaceous tap-rooted annual.

Classification: Cultivars of *Cannabis sativa*.

This cultivated line possesses intoxicating properties, and so the Subspecies *sativa* and its varieties (var. *sativa* and *spontanea*) are eliminated from consideration.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A new and distinct cultivar of *Cannabis* plant named 'GPZ', substantially as illustrated and described herein.

* * * * *